(12) United States Patent
Gibson et al.

(10) Patent No.: US 8,894,642 B2
(45) Date of Patent: Nov. 25, 2014

(54) IRRIGATED CATHETER

(75) Inventors: Charles A. Gibson, Malden, MA (US);
Gary S. Falwell, Moultonborough, NH
(US); Hab Seang, Dracut, MA (US)

(73) Assignee: Boston Scientific Scimed, Inc., Maple
Grove, MN (US)

( * ) Notice: Subject to any disclaimer, the term of this
patent is extended or adjusted under 35
U.S.C. 154(b) by 2357 days.

(21) Appl. No.: 11/596,722

(22) PCT Filed: May 17, 2005

(86) PCT No.: PCT/US2005/017581
§ 371 (c)(1),
(2), (4) Date: Sep. 26, 2008

(87) PCT Pub. No.: WO2005/112814
PCT Pub. Date: Jan. 12, 2005

(65) Prior Publication Data
US 2010/0152727 A1    Jun. 17, 2010

Related U.S. Application Data

(60) Provisional application No. 60/571,731, filed on May 17, 2004.

(51) Int. Cl.
*A61B 18/18* (2006.01)
*A61B 18/14* (2006.01)
*A61B 18/00* (2006.01)

(52) U.S. Cl.
CPC ... *A61B 18/1492* (2013.01); *A61B 2018/00029* (2013.01)
USPC .......................................................... 606/41

(58) Field of Classification Search
CPC .................. A61B 18/1492; A61B 2018/00029
USPC ..................................... 606/41; 607/115–116
See application file for complete search history.

(56) References Cited

U.S. PATENT DOCUMENTS 5,230,349 A    7/1993    Langberg
5,242,441 A    9/1993    Avitall
(Continued)

FOREIGN PATENT DOCUMENTS

EP    1008327    6/2000
JP    Hei 08-38503    2/1996
(Continued)

OTHER PUBLICATIONS

Chugh et al.; "Catheter Tip Orientation Affects Radiofrequency Ablation Lesion Size in the Canine Left Ventricle"; Pace, vol. 22, pp. 413-420.

(Continued)

*Primary Examiner* — Theodore Stigell
(74) *Attorney, Agent, or Firm* — Seager, Tufte & Wickhem, LLC

(57) ABSTRACT

Apparatus for irrigating an electrode of a catheter are disclosed. Among other things, a catheter is disclosed that comprises a shaft portion including a fluid passage to conduct fluid, an electrode coupled to a distal end of the shaft portion, and a handle portion coupled to a proximal end of the shaft portion. A portion of the fluid passage defines an opening in the shaft portion. The opening is constructed and arranged such that when fluid is conducted through the fluid passage, at least some of the fluid will contact the electrode after passing through the opening in the shaft portion.

13 Claims, 9 Drawing Sheets

(56) References Cited

U.S. PATENT DOCUMENTS

| | | |
|---|---|---|
| RE34,502 E | 1/1994 | Webster, Jr. |
| 5,334,193 A | 8/1994 | Nardella |
| 5,348,554 A | 9/1994 | Imran |
| 5,364,352 A | 11/1994 | Cimino et al. |
| 5,368,564 A | 11/1994 | Savage |
| 5,423,811 A | 6/1995 | Imran |
| 5,431,649 A | 7/1995 | Mulier |
| 5,445,148 A | 8/1995 | Jaraczewski et al. |
| 5,487,757 A | 1/1996 | Truckai et al. |
| 5,489,270 A | 2/1996 | van Erp |
| 5,545,161 A | 8/1996 | Imran |
| 5,562,619 A | 10/1996 | Mirarchi et al. |
| 5,582,609 A | 12/1996 | Swanson et al. |
| 5,609,151 A | 3/1997 | Mulier et al. |
| 5,611,777 A | 3/1997 | Bowden et al. |
| 5,658,278 A | 8/1997 | Imran |
| 5,697,927 A | 12/1997 | Imran et al. |
| 5,735,846 A | 4/1998 | Panescu et al. |
| 5,755,760 A | 5/1998 | Maguire et al. |
| 5,779,699 A | 7/1998 | Lipson |
| 5,782,760 A | 7/1998 | Schaer |
| 5,800,428 A | 9/1998 | Nelson |
| 5,827,272 A | 10/1998 | Breining et al. |
| 5,843,152 A | 12/1998 | Tu |
| 5,861,021 A | 1/1999 | Thome |
| 5,865,800 A | 2/1999 | Mirarchi et al. |
| 5,893,884 A | 4/1999 | Tu |
| 5,893,885 A | 4/1999 | Webster |
| 5,913,854 A | 6/1999 | Maguire |
| 5,938,603 A | 8/1999 | Ponzi |
| 5,954,719 A | 9/1999 | Chen |
| 5,980,516 A | 11/1999 | Mulier |
| 6,016,809 A | 1/2000 | Mulier |
| 6,032,077 A | 2/2000 | Pomeranz et al. |
| 6,053,912 A | 4/2000 | Panescu et al. |
| 6,063,080 A | 5/2000 | Nelson |
| 6,064,902 A | 5/2000 | Haissaguerre et al. |
| 6,083,222 A | 7/2000 | Klein et al. |
| 6,120,476 A | 9/2000 | Fung |
| 6,146,379 A | 11/2000 | Fleischman et al. |
| 6,156,027 A | 12/2000 | West |
| 6,171,275 B1 | 1/2001 | Webster |
| 6,171,305 B1 | 1/2001 | Sherman |
| 6,178,354 B1 | 1/2001 | Gibson |
| 6,196,916 B1 | 3/2001 | Childs |
| 6,210,406 B1 | 4/2001 | Webster |
| 6,217,573 B1 | 4/2001 | Webster |
| 6,217,574 B1 | 4/2001 | Webster |
| 6,226,554 B1 | 5/2001 | Tu et al. |
| 6,235,021 B1 | 5/2001 | Sieben |
| 6,236,224 B1 | 5/2001 | Schneider |
| 6,312,428 B1 | 11/2001 | Eggers et al. |
| 6,371,955 B1 | 4/2002 | Fuimaono |
| 6,447,507 B1 | 9/2002 | Bednarek |
| 6,458,123 B1 | 10/2002 | Brucker |
| 6,488,680 B1 | 12/2002 | Francischelli |
| 6,491,710 B2 | 12/2002 | Satake |
| 6,551,271 B2 | 4/2003 | Nguyen |
| 6,569,162 B2 | 5/2003 | He |
| 6,602,242 B1 | 8/2003 | Fung et al. |
| 6,605,055 B1 | 8/2003 | Sinofsky |
| 6,611,699 B2 | 8/2003 | Messing |
| 6,682,526 B1 | 1/2004 | Jones et al. |
| 7,727,230 B2 | 6/2010 | Fuimaono et al. |
| 2002/0198520 A1 | 12/2002 | Coen et al. |
| 2003/0028185 A1 | 2/2003 | He |
| 2003/0069570 A1 | 4/2003 | Witzel et al. |
| 2004/0054272 A1 | 3/2004 | Messing |
| 2005/0261754 A1* | 11/2005 | Woloszko ............ 607/99 |
| 2006/0253117 A1* | 11/2006 | Hovda et al. ........ 606/48 |
| 2006/0271036 A1* | 11/2006 | Garabedian et al. .... 606/41 |
| 2009/0054884 A1* | 2/2009 | Farley et al. ........ 606/15 |
| 2009/0137998 A1* | 5/2009 | Zikorus et al. ....... 606/15 |
| 2011/0022044 A1* | 1/2011 | Garabedian et al. .... 606/41 |

FOREIGN PATENT DOCUMENTS

| | | |
|---|---|---|
| JP | Hei 09-506808 | 7/1997 |
| JP | Hei 11-506947 | 6/1999 |
| JP | 2002-501769 | 1/2002 |
| WO | WO 03/082134 A1 | 10/2003 |
| WO | WO 2005/079901 A1 | 9/2005 |

OTHER PUBLICATIONS

Japanese Official Action dated Feb. 4, 2011 from corresponding Japanese Patent Application No. 2007-527444.
European Search Report dated Aug. 25, 2011 from corresponding European Patent Application No. 11168790.1.

* cited by examiner

IRRIGATED CATHETER

CROSS-REFERENCE TO RELATED APPLICATIONS

This application claims the benefit, under 35 U.S.C. §119 (e), of the filing date of U.S. provisional application Ser. No. 60/571,731 entitled "Irrigated Catheter," filed May 17, 2004, which is hereby incorporated herein by reference in its entirety.

FIELD OF INVENTION

The invention relates generally to methods and apparatus for irrigating an electrode of an electrophysiology catheter.

BACKGROUND

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multi-channel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

SUMMARY OF THE INVENTION

One embodiment of the invention is directed to an electrophysiology catheter comprising a shaft portion including a fluid passage to conduct fluid, an electrode coupled to a distal end of the shaft portion, and a handle portion coupled to a proximal end of the shaft portion. A portion of the fluid passage defines an opening in the shaft portion, and the opening is constructed and arranged such that when fluid is conducted through the fluid, at least some of the fluid will contact the electrode after passing through the opening in the shaft portion.

Another embodiment of the invention is directed to an electrophysiology catheter comprising a shaft portion comprising a fluid passage, a fluid reservoir coupled to the fluid passage, and a plurality of channels coupled to the fluid reservoir. The fluid passage has a first diameter and the reservoir has a second diameter that is larger than the first diameter. The electrophysiology catheter further comprises an electrode coupled to a distal end of the shaft portion and a handle portion coupled to a proximal end of the shaft portion. Each channel of the plurality of channels coupled to the fluid reservoir defines an opening in the shaft portion configured and arranged such that fluid exiting the channel through the opening will contact the electrode.

A further embodiment of the invention is directed to an electrophysiology catheter comprising a shaft portion comprising a fluid passage and a channel coupled to the fluid passage, wherein the channel defines an opening in the shaft portion. The electrophysiology catheter further comprises an electrode assembly coupled to the shaft portion and movable in a longitudinal direction along the shaft portion. The electrode assembly comprises an opening and is positionable such that fluid may flow from the channel through both the opening in the shaft portion and the opening in the electrode assembly. The electrophysiology catheter further comprises a handle portion coupled to a proximal end of the shaft portion.

BRIEF DESCRIPTION OF THE DRAWINGS

The accompanying drawings are not intended to be drawn to scale. In the drawings, each identical or nearly identical component that is illustrated in various figures is represented by a like reference character. For purposes of clarity, not every component may be labeled in every drawing. In the drawings.

DETAILED DESCRIPTION

To effectively treat a cardiac arrhythmia, a lesion having a sufficient size and depth must be created at a chosen location in the heart. It is known that for a given electrode size and tissue contact area, the size of a lesion created by radio frequency (RF) energy is a function of the RF power level and exposure time. At higher power levels, however, the exposure time can be limited by an increase in impedance that occurs when the temperature at the electrode-tissue interface approaches 100° C. One way of maintaining the temperature at the electrode-tissue interface below or equal to this limit is to irrigate the ablation electrode with an irrigation fluid such as saline. The saline provides convective cooling, which controls the electrode-tissue interface temperature and thereby prevents an increase in the impedance. Various embodiments of a catheter having an irrigated ablation electrode will now be described.

Figure 1A:
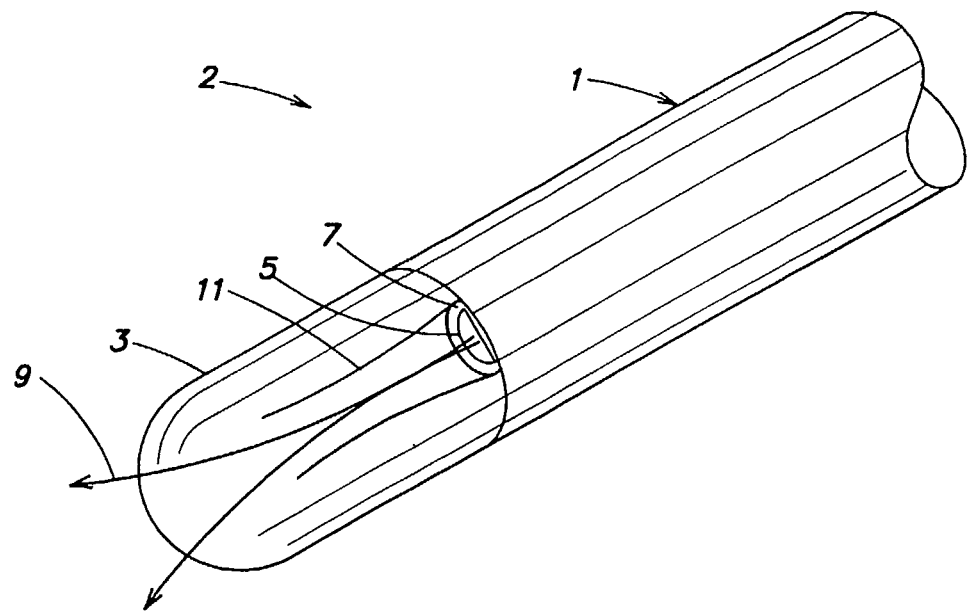
FIG. 1A illustrates a portion of a catheter according to one embodiment of the invention.
Figure 1B:
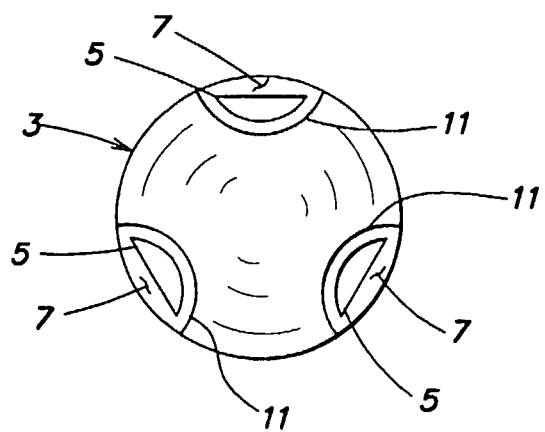
FIG. 1B illustrates a view of the distal end of the catheter shown in FIG. 1A.

FIGS. 1A and 1B illustrate a first embodiment of the invention. FIG. 1A illustrates a catheter 2 comprising a shaft 1 having an ablation electrode 3 coupled at a distal end thereof. The shaft 1 includes an opening 5 on a distally facing surface 7 of the shaft 1. A fluid 9, such as saline, may be released from the shaft 1 via opening 5 and may be directed towards the electrode 3 to promote convective cooling of the electrode 3. A groove 11 is included on a portion of electrode 3 that is adjacent to the opening 5 so as to channel fluid exiting opening 5 along the electrode 3. The groove 11 may be configured such that the fluid 9 is directed towards portions of the electrode 3 where cooling is desired.

FIG. 1B illustrates a view of the distal end of the catheter 2. As shown, three openings 5 are included on the distal facing surface 7 of the shaft 1, and three corresponding grooves 11 are included on the electrode 3 adjacent openings 5. However, it should be appreciated that the invention is not limited in this respect, and that different numbers of grooves and/or openings (e.g., two, four, five, six, or some other number of grooves/openings) may alternatively be used. Further, the number of grooves 11 and openings 5 need not be the same. For example, no grooves need be included on the electrode 3. In addition, the illustrated configurations of openings 5 and grooves 11 are merely exemplary. Although openings 5 are shown as semicircular, these openings may alternatively be circular, linear, oval, or another suitable shape. In addition, while groove 11 is shown as having a generally semicircular cross section, the groove 11 may assume other configurations. Specifically, the groove 11 need not be uniform along the length of electrode 3. For example, only a proximal portion of electrode 3 may include grooves, while a distal portion of the electrode 3 may include no grooves.

Figure 2A:
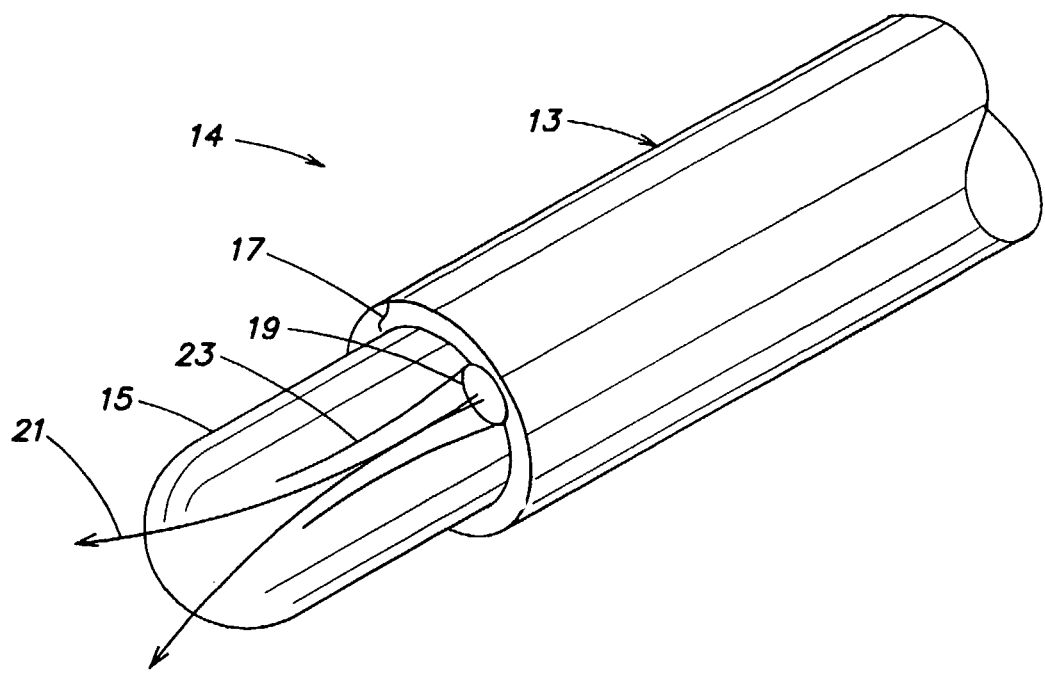
FIG. 2A illustrates a portion of a catheter according to another embodiment of the invention.
Figure 2B:
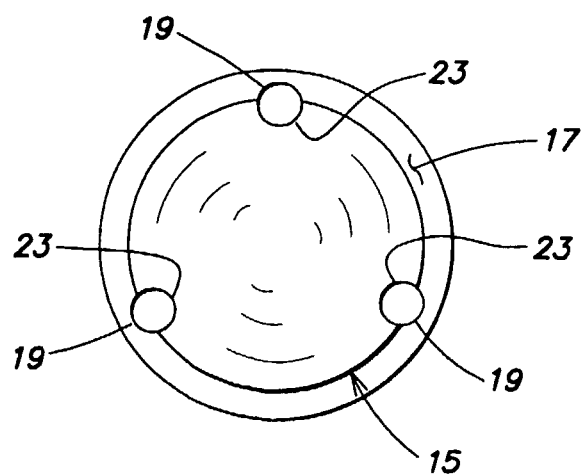
FIG. 2B illustrates a view of the distal end of the catheter shown in FIG. 2A.

FIGS. 2A and 2B illustrate another embodiment of the invention. As shown in FIG. 2A, catheter 14 comprises a shaft 13 and an electrode 15 coupled at a distal end thereof. Shaft 13 has a larger diameter than that of electrode 15. Thus, shaft 13 includes a distal facing surface 17 at the interface of the shaft 13 and electrode 15. An opening 19 is provided on the surface 17 from which fluid 21 may be released. The fluid 21 may be channeled by a groove 23 on the electrode 15 to direct the fluid 21 towards desired portions of the electrode 15.

FIG. 2B illustrates a view of the distal end of the catheter 14. As shown, three openings 19 are included on the distal facing surface 17 of the shaft 13, and three corresponding grooves 23 are included on the electrode 15 adjacent openings 19. As with the embodiment of FIGS. 1A-1B, it should be appreciated that the number of grooves 23 and openings 19 illustrated in FIGS. 2A-2B, and the configurations of such grooves and openings, is merely exemplary and that other implementations are possible.

Figure 3A:
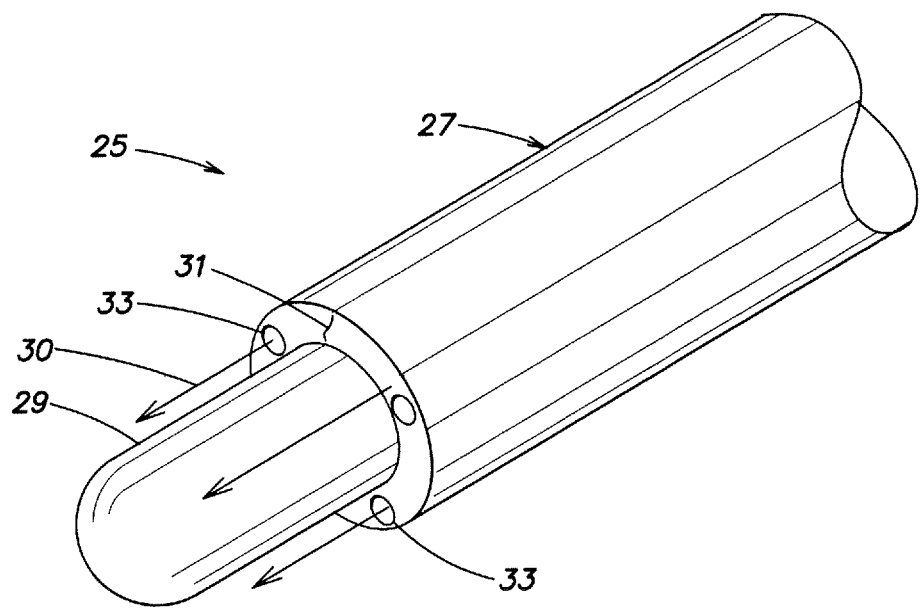
FIG. 3A illustrates a portion of a catheter according to another embodiment of the invention.
Figure 3B:
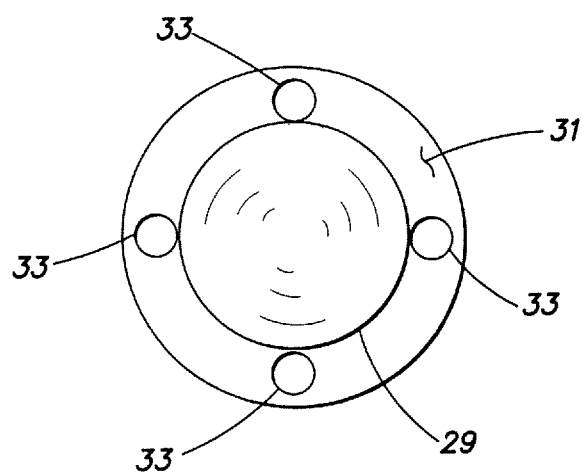
FIG. 3B illustrates a view of the distal end of the catheter shown in FIG. 3A.

FIGS. 3A and 3B illustrate a further embodiment of the invention. The embodiment of FIGS. 3A and 3B is similar to that of FIGS. 2A and 2B, except that the openings that are provided for the release of irrigation fluid are located on the catheter shaft at a radius outside that of the ablation electrode. FIG. 3A illustrates a catheter 25 comprising a shaft 27 and an ablation electrode 29 coupled at a distal end thereof. A distal facing surface 31 of the catheter shaft 27 includes a plurality of openings 33 that release fluid 30 about ablation electrode 29. Although electrode 29 is not shown as including any grooves, grooves may be included on the electrode 29 to direct the fluid released from openings 33, if desired.

FIG. 3B illustrates a view of the distal end of the catheter 14. As shown, four circular openings 33 are included on the distal facing surface 31 of the shaft 27. However, the number of openings 19 and the configuration of the openings 19 shown in FIG. 3B is merely exemplary. For example, a different number of openings or differently shaped openings may alternatively be provided in accordance with this embodiment.

Figure 4:
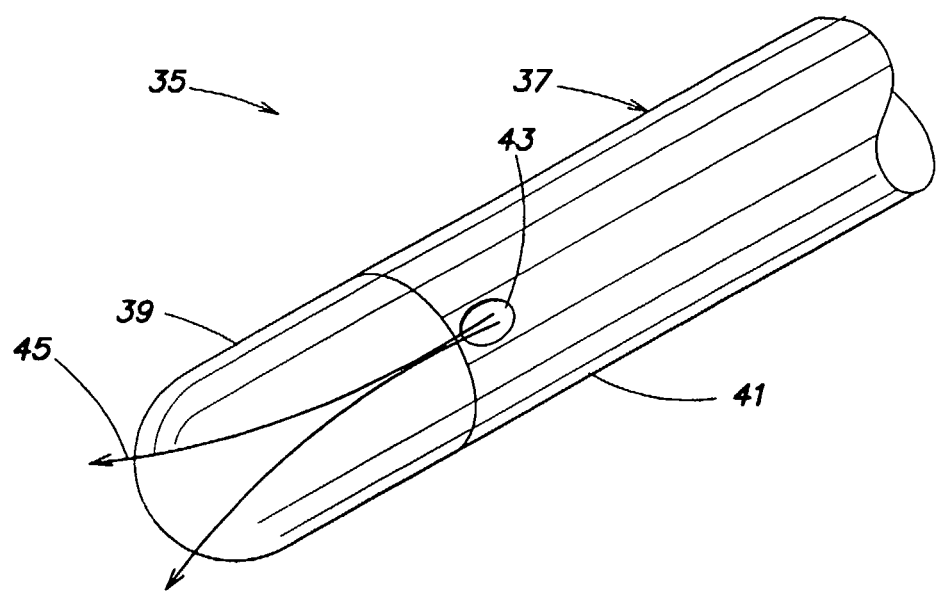
FIG. 4 illustrates a portion of a catheter according to another embodiment of the invention.

FIG. 4 illustrates another embodiment of the invention. According to this embodiment, fluid openings are provided in the portion of the surface of the catheter shaft that is substantially cylindrical. FIG. 4 illustrates a catheter 35 including a shaft 37 having an ablation electrode 39 at a distal end thereof. Electrode 39 has a diameter that is approximately equal to a diameter of the shaft 37. Shaft 37 includes an outer surface 41 having a substantially cylindrical shape. An opening 43 is provided in the surface 41 for the release of irrigation fluid 45. The opening 43 may be configured such that the irrigation fluid 45 is generally directed towards the distal end of catheter 35 (i.e., towards ablation electrode 39). If desired, grooves may also be included in the ablation electrode 39 to direct the irrigation fluid 45 as it exits opening 43.

Figure 5A:
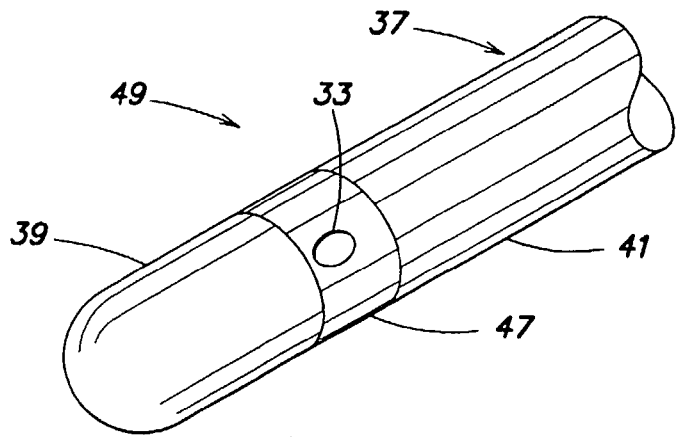
FIGS. 5A-C illustrate one exemplary method for constructing a catheter in accordance with the embodiment of FIG. 4.
Figure 5B:
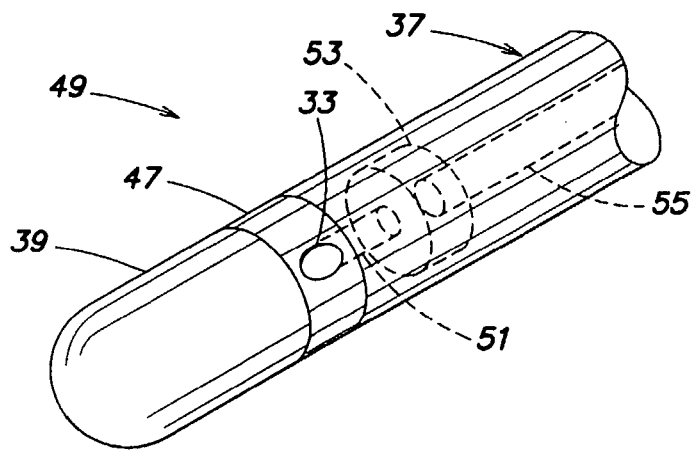
Figure 5C:
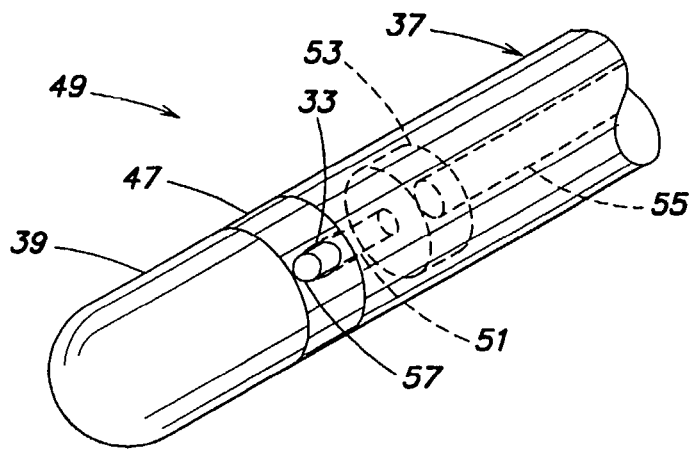

FIGS. 5A-5C illustrate one exemplary method for constructing a catheter in accordance with the embodiment of FIG. 4. The catheter 49 of FIG. 5A is substantially the same as the catheter 35 of FIG. 4, however, a distal portion 47 of the shaft 37 is formed of epoxy. As shown in FIG. 5B, a channel 51 in the distal portion 47 of the shaft 37 is coupled between an opening 33 in the shaft and a reservoir 53 disposed within the shaft. The reservoir 53 is in turn coupled to a fluid lumen 55 disposed along a central longitudinal axis of the catheter 49.

The fluid lumen 55 may conduct irrigation fluid (e.g., saline) into reservoir 53, and fluid may exit the shaft 37 from the reservoir 53 via the channel 51 and opening 33. It should be appreciated that while only one channel 51 and corresponding opening 33 is shown in catheter 49, a plurality of channels 51 and corresponding openings 33 may be provided. For example, a plurality of channels 51 may be coupled to the reservoir 53 and may be associated with corresponding openings 33 in the outer surface 41 of the shaft 37. Although not illustrated, it should be appreciated that a catheter handle may be provided at a proximal end of the shaft 37. Fluid may be introduced into the fluid lumen 55, for example, via a port provided on or near the handle. In addition, while only a single fluid lumen 55 is illustrated, a plurality of fluid lumens may be used to conduct fluid to openings 33. For example, each opening 33 may be associated with a corresponding fluid lumen that runs the length of the shaft 37, and reservoir 53 may be eliminated.

The distal portion 47 of shaft 37 may function to attach the electrode 39 to the remainder of the shaft 37. In addition, the distal portion 47 may be moldable such that channels 51 may be formed therein. It should be appreciated that while the distal portion 47 is described as being formed of epoxy, other adhesive materials through which channels may be formed may also be suitable. FIG. 5C illustrates a method of forming the channel 51 in the distal portion 47 of shaft 37. In particular, FIG. 5C illustrates a cylindrical rod 57 that may be used to form channels in the epoxy of distal portion 47. The rod 57 may be disposed within distal portion 47, between the reservoir 53 and the exterior of the shaft 37, during hardening of the epoxy used to form the distal portion 47. It should be appreciated that the rod 57 may be solid or have a tubular shape or have any other configuration that enables channels 51 to be formed.

Figure 6A:
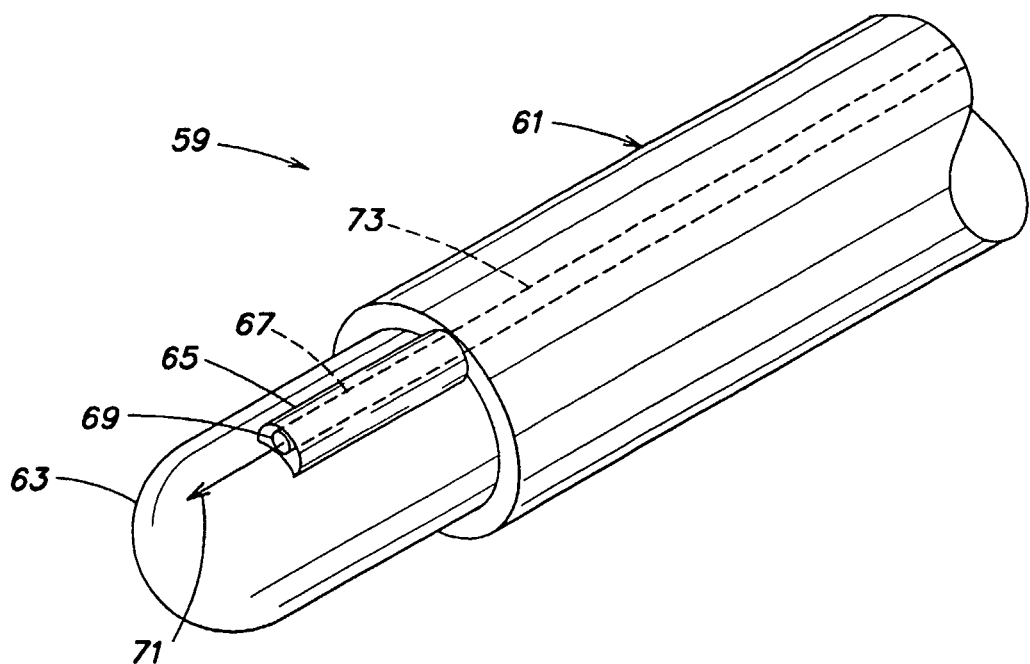
FIG. 6A illustrates a portion of a catheter according to another embodiment of the invention.
Figure 6B:
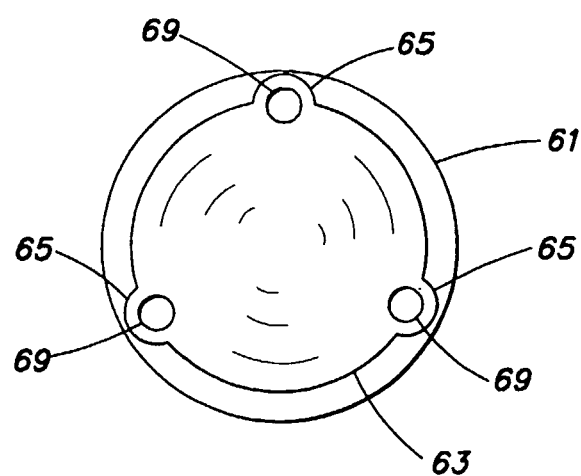
FIG. 6B illustrates a view of the distal end of the catheter shown in FIG. 6A.

FIGS. 6A and 6B illustrate a further embodiment of the invention. According to this embodiment, the ablation electrodes includes protrusions, each having a fluid channel therein. FIG. 6A illustrates a catheter 59 comprising a shaft 61 and an ablation electrode 63 coupled at a distal end thereof. The electrode 63 includes a plurality of protrusions 65, each having an irrigation channel 67 therein. Each irrigation channel 67 defines an opening 69 at a surface of the electrode 63. The openings 69 release fluid 71 about the ablation electrode 63. Although electrode 63 is not shown as including any grooves, grooves may be included on the electrode 63 to direct the fluid released from the openings 69, if desired. Each irrigation channel 67 in electrode 63 may be coupled to a fluid lumen 73 in shaft 61 (as shown for one fluid lumen 73 in FIG. 6A). Fluid lumen 73 conducts fluid along the length of the catheter shaft 61 to the ablation electrode 63.

FIG. 6B illustrates a view of the distal end of the catheter 59. As shown, three protrusions 65 and three corresponding openings 69 are included on the ablation electrode 63. However, the number of openings 63 and protrusions 65 shown is merely exemplary. Moreover, the configuration of the openings 63 and protrusions 65 shown in FIG. 6B is merely exemplary. For example, a different number of openings and/or protrusions and differently shaped openings and/or protrusions may alternatively be provided in accordance with this embodiment.

FIGS. 7-10 illustrate embodiments of the invention that include an irrigated movable electrode. FIGS. 7A and 7B illustrate a side view and top view of a catheter 77 comprising a shaft 79 and an ablation electrode 81 movably coupled to the shaft 79. For example, the electrode 81 may be slid longitudinally along the shaft 79. Exemplary mechanisms for moving the electrode are described in U.S. Pat. No. 6,178,354 to Gibson, U.S. Pat. No. 6,461,356 to Patterson, and U.S. Pat. No. 6,464,698 to Falwell, each of which is assigned to C.R. Bard Inc. and incorporated herein by reference. The shaft 79 includes a fluid lumen 87 that conducts fluid along the length of the catheter shaft 79. The shaft 79 further includes a plurality of irrigation channels 85 coupled to the fluid lumen 87. Each irrigation channel 85 defines an opening 83 at a surface of the shaft 79. The openings 83 release fluid 89 along the shaft 79 and about the ablation electrode 81. Electrode 81 may be solid such that the openings 83a obscured by electrode 81 at a given position of the electrode do not release fluid. Alternatively, electrode may be hollow such that the openings 83a obscured by electrode 81 at a given position of the electrode release fluid into the electrode to cool the electrode from within. The fluid may also be withdrawn from the electrode (e.g., via a movable lumen coupled thereto) as in "closed circuit" cooled electrode configurations.

Figure 7A:
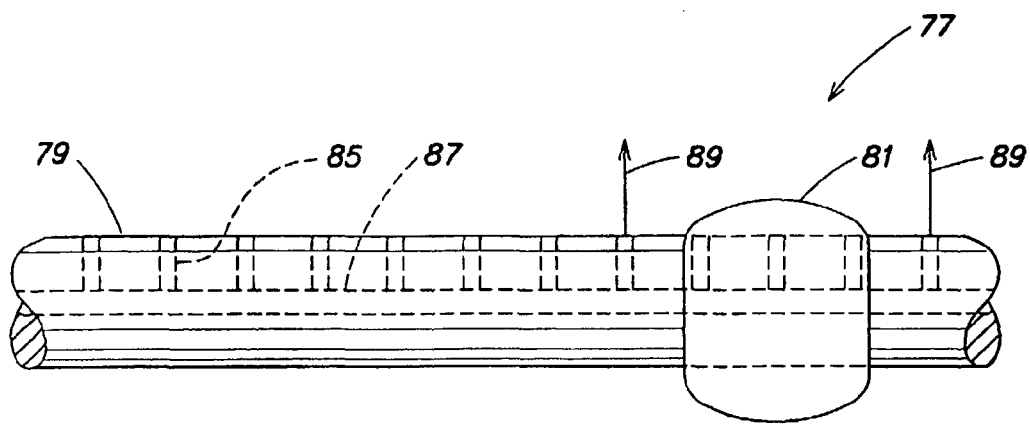
FIG. 7A illustrates a side view of portion of a catheter according to a further embodiment of the invention.
Figure 7B:
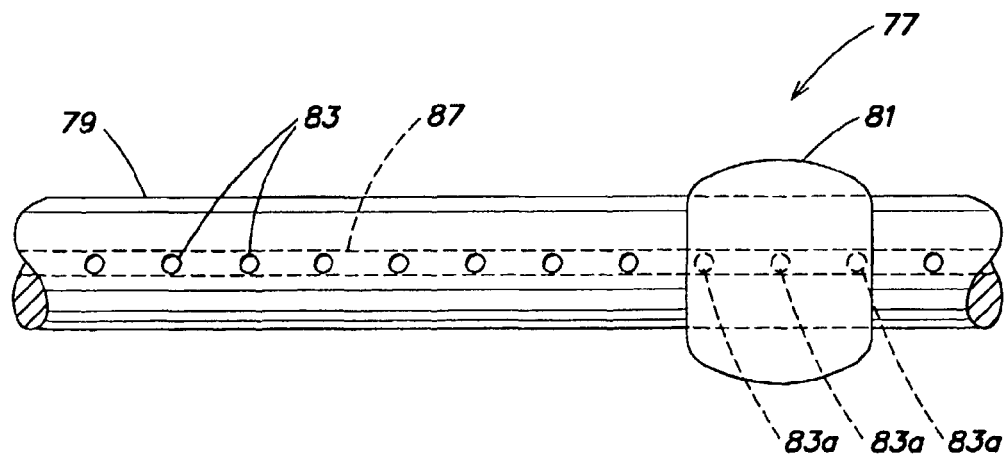
FIG. 7B illustrates top view of the distal end of the catheter shown in FIG. 7A.
Figure 8A:
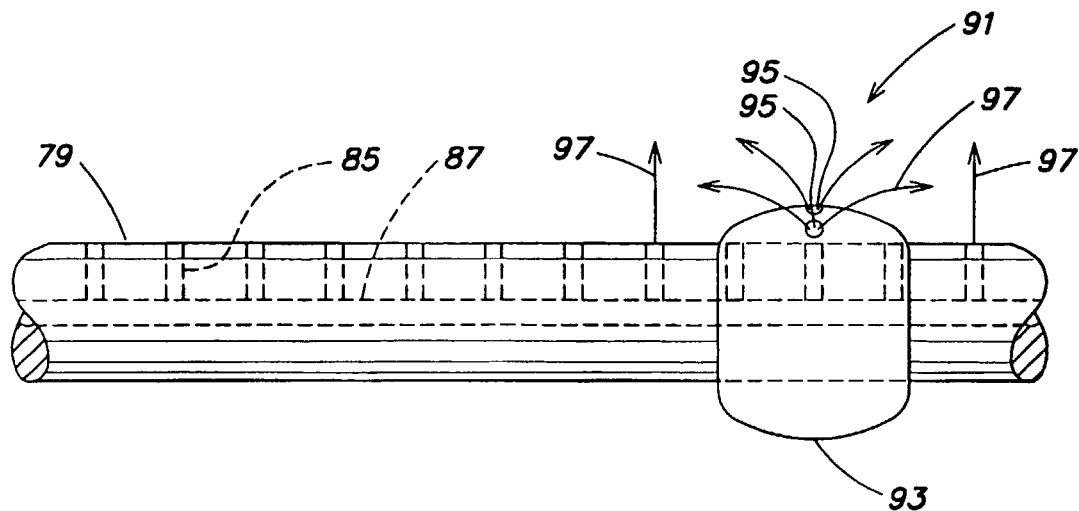
FIG. 8A illustrates a side view of a portion of a catheter according to another embodiment of the invention.
Figure 8B:
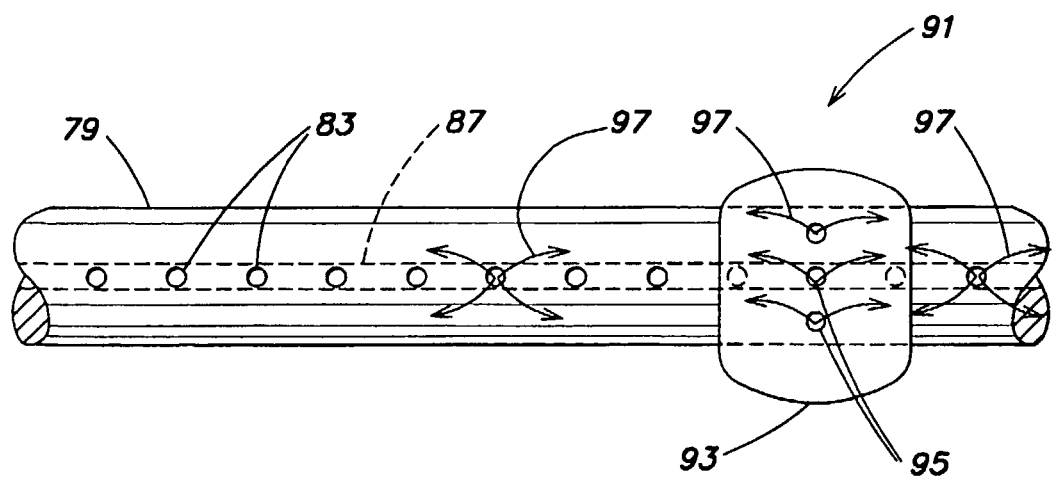
FIG. 8B illustrates top view of the distal end of the catheter shown in FIG. 8A.

FIGS. 8A and 8B illustrate an embodiment of the invention that is similar to the embodiment of FIGS. 7A and 7B, but wherein the movable electrode includes openings for the release of irrigation fluid. Catheter 91 comprises a shaft 79 and an ablation electrode 93 movably coupled to the shaft 79 in the manner discussed in connection with FIGS. 7A-7B. The shaft 79 includes a fluid lumen 87 that conducts fluid along the length of the catheter shaft 79, and a plurality of irrigation channels 85 coupled to the fluid lumen 87. Each irrigation channel 85 defines an opening 83 at a surface of the shaft 79. The openings 83 release fluid 97 along the shaft 79 and about the ablation electrode 93. Electrode 93 also includes openings 95 that release fluid 97 about the ablation electrode. Electrode 93 may be hollow such that fluid 97 passes through openings 83 in the shaft into the electrode 93 and then exits through openings 95 in the electrode 93. Alternatively, channels in the electrode 93 may correspond with channels in the shaft 79 such that when the electrode 93 is properly positioned, fluid flows from the channels 85 in the shaft into channels in the electrode 93 that are coupled to openings 95. The openings 95 in the electrode 93 may assume a number of different configurations. The openings 95 may be included about the circumference of the electrode 93 or on one side of the electrode 93. The openings 95 may also be in any pattern or number on the electrode 93.

Figure 9:
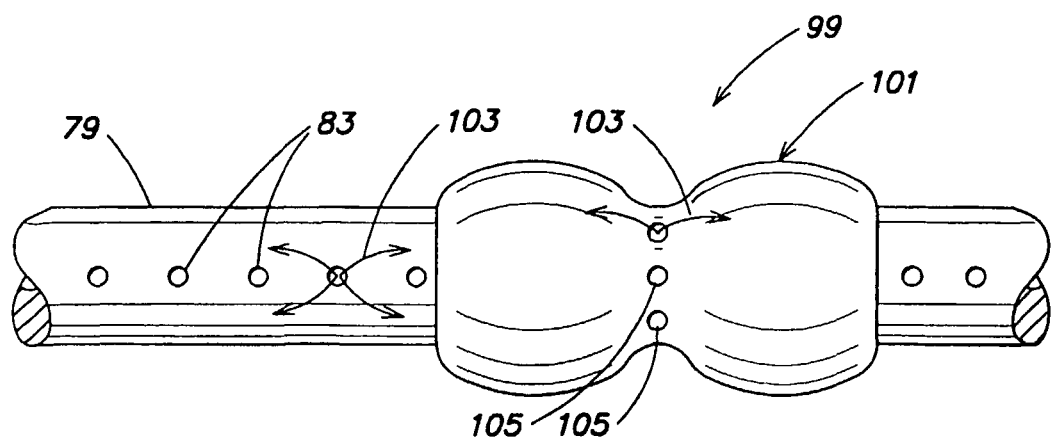
FIG. 9 illustrates a portion of a catheter according to another embodiment of the invention.
Figure 10:
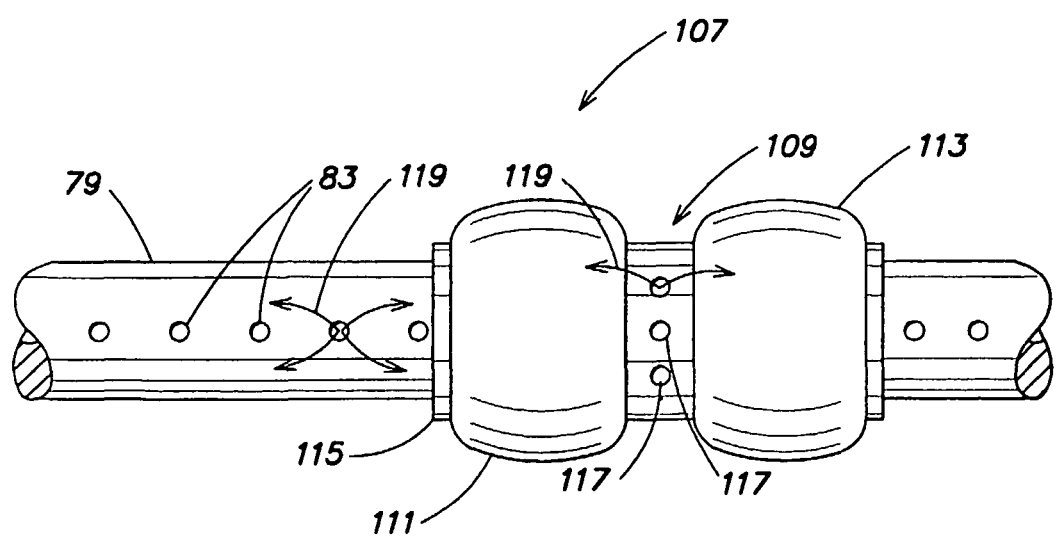
FIG. 10 illustrates a portion of a catheter according to another embodiment of the invention.

FIGS. 9 and 10 illustrate further embodiments of a catheter comprising a movable electrode. The catheters of FIGS. 9 and 10 are operable in substantially the same manner as the catheter of FIGS. 8A and 8B, but include electrodes having different configurations than that of FIGS. 8A and 8B. The catheter 99 of FIG. 9 comprises a shaft 79 and an ablation electrode 101 movably coupled to the shaft 79 in the manner discussed in connection with FIGS. 7A-7B. Electrode 101 has a dumbbell shape such that the diameters of the electrode at the longitudinal ends of the electrode are greater than the diameter at the center of the electrode. The shaft 79 includes a plurality of openings 83 that release fluid 103 along the shaft 79 and about the ablation electrode 101. Electrode 101 also includes openings 105 that release fluid 103 about the ablation electrode 101. Electrode 101 may be hollow such that fluid 103 passes through openings 83 in the shaft 79 into the electrode 101 and then exits through openings 105 in the electrode 101. Alternatively, channels in the electrode 101 may correspond with channels in the shaft 79 such that when the electrode 101 is properly positioned, fluid flows from the channels in the shaft into channels in the electrode 101 that are coupled to openings 105. The openings 105 in the electrode 101 may assume a number of different configurations. The openings 105 may be included about the circumference of the electrode 101 or on one side of the electrode 101. The openings 105 may also be in any pattern or number on the electrode 101.

The catheter 107 of FIG. 10 comprises a shaft 79 and an electrode assembly 109 movably coupled to the shaft 79 in the manner discussed in connection with FIGS. 7A-7B. Electrode assembly 109 comprises electrodes 111 and 113 coupled to a sleeve 115. One or both of electrodes 111 and 113 may be ablation electrodes. At least one electrode may be a mapping electrode. The sleeve 115 includes openings 117 between electrodes 111 and 113 that release fluid between the electrodes. The shaft 79 includes a plurality of openings 83 that release fluid 103 along the shaft 79 and about the electrode assembly 109. A portion of sleeve 115 may form a reservoir about the shaft 79 such that fluid 119 passes through openings 83 in the shaft 79 into the reservoir then exits through the openings 117 in the sleeve 115. Alternatively, channels in the sleeve 115 may correspond with channels in the shaft 79 such that when the sleeve 115 is properly positioned, fluid flows from the channels in the shaft into channels in the sleeve 115 that are coupled to openings 117. The openings 117 in the sleeve 115 may assume a number of different configurations. The openings 117 may be included about the circumference of the sleeve 115 or on one side of the sleeve 115. The openings 117 may also be in any pattern or number on the sleeve 115.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An electrophysiology catheter, comprising:
   a shaft portion comprising a fluid passage and a channel coupled to the fluid passage, wherein the channel defines an opening in the shaft portion;
   an electrode assembly coupled to the shaft portion and movable in a longitudinal direction along the shaft portion, wherein the electrode assembly comprises an opening, and wherein the electrode assembly is positionable such that fluid may flow from the channel through both the opening in the shaft portion and the opening in the electrode assembly; and
   a handle portion coupled to a proximal end of the shaft portion.

2. The catheter of claim 1, wherein the electrode assembly comprises an electrode, and wherein the opening in the electrode assembly is formed in the electrode.

3. The catheter of claim 2, wherein the electrode is generally dumbbell-shaped.

4. The catheter of claim 2, wherein the electrode comprises a first portion having a first diameter, a second portion having a second diameter, and a third portion located between the first and second portions and having a third diameter that is smaller than each of the first and second diameters, and wherein the opening is formed in the third portion.

5. The catheter of claim 1, wherein the electrode assembly comprises a sleeve portion and a plurality of electrodes coupled thereto, and wherein the opening is formed in the sleeve portion.

6. The catheter of claim 1, wherein the electrode assembly consists of an electrode.

7. A method of irrigation using a catheter, the catheter comprising a shaft portion and an electrode assembly movably coupled to the shaft portion, wherein the shaft portion comprises a first opening and the electrode assembly comprises a second opening, the method comprising an act of:
   irrigating a region adjacent the electrode assembly by causing fluid to flow through the second opening via the first opening.

8. The method of claim 7, further comprising an act of:
   moving the electrode assembly in a longitudinal direction along the shaft portion.

9. The method of claim 7, wherein the electrode assembly comprises an electrode, and wherein the second opening is formed in the electrode.

10. The method of claim 9, wherein the electrode is generally dumbbell-shaped.

11. The method of claim 10, wherein the electrode comprises a first portion having a first diameter, a second portion having a second diameter, and a third portion located between the first and second portions and having a third diameter that is smaller than each of the first and second diameters, and wherein the second opening is formed in the third portion.

12. The catheter of claim 7, wherein the electrode assembly comprises a sleeve portion and a plurality of electrodes coupled thereto, and wherein the second opening is formed in the sleeve portion.

13. The catheter of claim 7, wherein the electrode assembly consists of an electrode.

* * * * *